(12) United States Patent
Delfourne et al.

(10) Patent No.: US 6,583,150 B1
(45) Date of Patent: Jun. 24, 2003

(54) PHARMACEUTICAL COMPOSITION BASED ON POLYAROMATIC COMPOUNDS

(75) Inventors: Evelyne Delfourne, Pollestres (FR); Nathalie Bontemps-Subielos, Saint-Cyprien Plage (FR); Francis Darro, Brussels (BE); Jean Bastide, Perpignan (FR); Robert Kiss, Wauthier-Braine (BE); Armand Frydman, Verrieres le Buisson (FR)

(73) Assignee: Laboratorie L. Lafon, Maisons Alfort (FR)

( * ) Notice: Subject to any disclaimer, the term of this patent is extended or adjusted under 35 U.S.C. 154(b) by 0 days.

(21) Appl. No.: 09/936,842

(22) PCT Filed: Mar. 17, 2000

(86) PCT No.: PCT/FR00/00672

§ 371 (c)(1), (2), (4) Date: Sep. 18, 2001

(87) PCT Pub. No.: WO00/55160

PCT Pub. Date: Sep. 21, 2000

(30) Foreign Application Priority Data

Mar. 18, 1999 (FR) .............................................. 99 03390

(51) Int. Cl.[7] .................. A61K 31/4738; C07D 471/12; C07D 471/02
(52) U.S. Cl. ........................... 514/280; 546/48; 546/81; 546/88; 514/292
(58) Field of Search ................................. 514/280, 292; 546/48, 81, 88

(56) References Cited

U.S. PATENT DOCUMENTS 5,182,287 A    1/1993    Gunawardana et al.

FOREIGN PATENT DOCUMENTS

| GB | 0 695 752 A1 | 2/1996 |
| WO | WO 98/49165 | 11/1998 |
| WO | WO 99/59996 | 11/1999 |

OTHER PUBLICATIONS

Kitahara, Y. et al.: Synthesis of Meridine, Cystodamine, and related compounds including Iminoquinolinequinone structure. Tetrahedron, vol. 54, pp. 8421–8432, 1998.*

Bontemps et al., XP–002125108, "*Cystodamine, A New Cytotoxic Fused Polyaromic Alkaloid from the Mediterranean Ascidian Cystodytes Delle Chiajei*", vol. 35, No. 38, pps. 7023–7026.

* cited by examiner

*Primary Examiner*—Charanjit S. Aulakh
(74) *Attorney, Agent, or Firm*—Young & Thompson

(57) ABSTRACT

A pharmaceutical composition comprising an efficient amount of a compound selected among the compounds of formulae (I) and (II). The compounds have useful cytotoxic properties providing therapeutic application as antitumoral medicine.

9 Claims, No Drawings

PHARMACEUTICAL COMPOSITION BASED ON POLYAROMATIC COMPOUNDS

This application is a 371 of PCT/FR00/00672 filed Mar. 17, 2000, now WO00/55160 Sep. 21, 2000.

The present invention relates to pharmaceutical composition based on polyaromatic compounds which are useful in particular as antitumor medicinal products.

In 1999, the cytotoxic treatments (chemotherapy) used to reduce the size of cancer tumors, to contain the development of the tumoral process or even, in all too few cases, to eliminate lumps of cancer cells and the risk of metastases, combine chemical substances recently introduced with others which have been used for a few decades. For example, 5-fluorouracil (5-FU), which has been known for nearly 40 years as one of the most active treatments for colorectal cancer, may be replaced with one or other of the inhibitors specific for topoisomerase I (irinotecan or topotecan) when the tumor is no longer sensitive to 5-FU. More generally, the therapeutic arsenal available for treating colorectal cancers is also enriched by the availability of oxaliplatin, novel in situ "donors" of 5-FU or selective inhibitors of thymidylate synthase. This co-existence is not limited to the treatment of colorectal cancers since, in addition, the chemotherapy of breast, ovarian and lung cancers now makes wide use of the family of taxane derivatives (paclitaxel and docetaxel). The need for more effective and better-tolerated treatments, thus improving the survival and quality of life of the patients, is imperative since, again taking the example of colorectal tumors, it has been estimated (S. L. Parker, T. Tong, S. Bolden et al., CA Cancer J. Clin., 1997) that, in the United States alone, more than 131 000 new cases were diagnosed in 1997, of which 54 000 were responsible for the death of the patients. It is the awareness of this situation which has incited the inventors to focus their attention on a family of polyaromatic compounds that have as yet been little studied, identified in Ascidians of warm seas, to develop a novel medicinal chemistry intended to select synthetic compounds derived from chemical design/modulation research and endowed with significant therapeutic cytotoxic activity.

The seas and oceans which cover more than 70% of the world's surface are home to marine plants and sponges whose progressive systematic pharmacognosic study shows that these living species may contain complex alkaloids with advantageous pharmacological properties. For example, the sponges *Cryptotheca crypta* and *Halichondria okadai* have been the subject of in-depth research since the discovery of the presence, in their cells, of cytarabin or of halichondrin B. This is likewise the case for the family of tunicates, since the isolation of aplidin from the tunicate *Aplidium albicans* which lives in the Balearic islands (Spain) Alkaloids of tetrahydroisoquinolone structure have been isolated from the ascidian *Ecteinascidia turbinata*. Among these, ecteinascidin-743 has been the subject of in-depth preclinical studies (E. Igbicka et al., NCI-EORTC symposium, 1998; Abst. 130 p. 34), and also of clinical tests intended to define its therapeutic potential as an anticancer medicinal product (A. Bowman et al., NCI-EORTC symposium, 1998; Abst. 452 p. 118; M. Villanova-Calero et al., NCI-EORTC symposium, 1998; Abst. 453 p. 118; M. J. X. Hillebrand et al., NCI-EORTC symposium, 1998; Abst. 455 p. 119; E. Citkovic et al., NCI-EORTC symposium, 1998; Abst. 456 p. 119). Novel pentacyclic acridine derivatives have also formed the subject of pharmacochemical studies (D. J. Hagan et al., J. Chem. Soc., Perkin Transf., 1997; 1: 2739–2746).

Among these compounds, mention may be made of meridine, an natural alkaloid extracted from the ascidian *Amphicarpa meridiana* or from the marine sponge Corticum sp. Meridine was isolated by Schmitz et al. (J. Org. Chem. 1991; 56: 804–808) and then described for its antiproliferative properties on a model of murine leukemia (P388) and its antifungal properties in patent U.S. Pat. No. 5,182,287 (Gunawardana et al. of Jan. 23, 1993). Its antifungal properties were described by McCarthy et al. (J. of Nat. Products 1992; 55: 1664–1668) along with its cytotoxic properties on two human cell lines: colon cancer cells (HT-29) and lung carcinoma cells (A549), which were reported by Longley et al. (J. of Nat. Products 1993; 56: 915–920). The synthesis of meridine has been carried out according to various processes by Kitahara et al. (Chem. Pharm. Bull 1994; 42: 1363–1364), Bontemps et al. (Tetrahedron 1997; 37: 1743–1750) and Kitahara et al. (Tetrahedron 1998; 54: 8421–8432).

Among these compounds, mention may also be made of cystodamine, a pentacyclic alkaloid isolated from the Ascidian *Cystodytes dellechiajei* by Bontemps et al. (Tetrahedron lett., 1994; 35: 7023–7026) which has activity on human leukemia lymphoblasts.

The subject of the present invention is a pharmaceutical composition comprising an effective amount of a compound chosen from the compounds of formulae:

Formula I

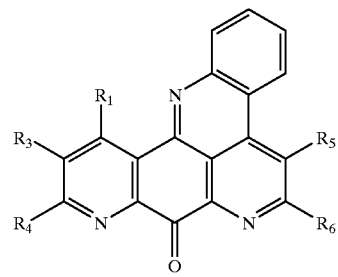

Formula II

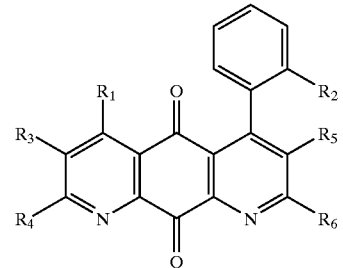

in which:
R$_1$, R$_3$, R$_4$, R$_5$ and R$_6$ are chosen from hydrogen, halogens and hydroxyl, —CHO, —OR, —COOH, —CN, —CO$_2$R, —CONHR, —CONRR',

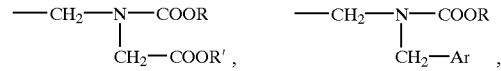

—NH$_2$, —NHR, —N(R)$_2$, —NH—CH$_2$—CH$_2$—N(CH$_3$)$_2$, —NHCOR, morpholino, nitro and —SO$_3$H groups,
R and R' being chosen from C$_1$–C$_6$ alkyl groups and Ar being a C$_6$–C$_{14}$ aryl group,
R$_2$ is chosen from nitro and —NHCOCF$_3$ groups,
and the addition salts of these compounds with pharmaceutically acceptable acids.

A subject of the present invention is, more particularly, compounds chosen from the compounds of formula I and of formula II in which:

$R_1$, $R_3$ and $R_4$ are chosen from hydrogen, halogens, hydroxyl, —CHO, —OR, —COOH, —CN, —$CO_2R$, —CONHR, —CONRR', —$NH_2$, —NHR, —$N(R)_2$, —NH—$CH_2$—$CH_2$—$N(CH_3)_2$, —NHCOR, morpholino, nitro and —$SO_3H$ groups, $R_2$ is chosen from nitro and —$NHCOCF_3$ groups, and the addition salts of these compounds with pharmaceutically acceptable acids.

In one preferred embodiment, a subject of the invention is a pharmaceutical composition comprising an effective amount of a compound chosen from the compounds of formula I in which $R_1$ is chosen from hydrogen and methoxy and —$N(CH_3)_2$ groups and the compounds of formula II in which $R_1$ is chosen from hydrogen and methoxy, $N(CH_3)_2$ and —$NHCOCH_3$ groups and $R_2$ is an —$NHCOCF_3$ group, and the addition salts of these compounds with pharmaceutically acceptable acids.

In another form, a subject of the invention is a pharmaceutical composition comprising an effective amount of a compound chosen from the compounds of formula I in which $R_3$ is a —COOEt group and the compounds of formula II in which $R_3$ is a —COOEt group and $R_2$ is chosen from —$NHCOCF_3$ and —$NO_2$ groups, and the addition salts of these compounds with pharmaceutically acceptable acids.

In another form, a subject of the invention is a pharmaceutical composition comprising an effective amount of a compound chosen from the compounds of formula I in which $R_4$ is a methoxy group and the compounds of formula II in which $R_4$ is a methoxy group and $R_2$ is chosen from —$NHCOCF_3$ and —$NO_2$ groups, and the addition salts of these compounds with pharmaceutically acceptable acids.

The expression "addition salts with pharmaceutically acceptable acids" denotes salts which give the biological properties of the free bases, without having an adverse effect. These salts may be, in particular, those formed with mineral acids, such as hydrochloric acid, hydrobromic acid, sulfuric acid, nitric acid or phosphoric acid; acidic metal salts, such as disodium orthophosphate and monopotassium sulfate, and organic acids.

In general, the compounds of formulae I and II are obtained according the general reaction scheme described by Kitahara et al. (Chem Pharm. Bull 1994; 42: 1363–1364) and Kitahara et al. (Tetrahedron 1998; 54: 8421–8432). According to this scheme, the compounds of formula II may be prepared by a hetero Diels-Alder reaction between a quinoline-5,8-dione substituted in position 4 and a substituted aza-diene, followed by dehydrogenation of the intermediate dihydrogenated compound. The compounds of formula I are prepared from the compounds of formula II by cyclization:

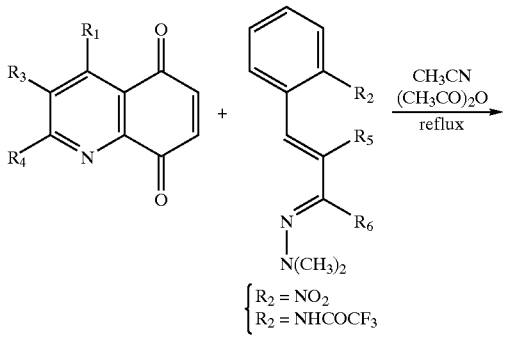

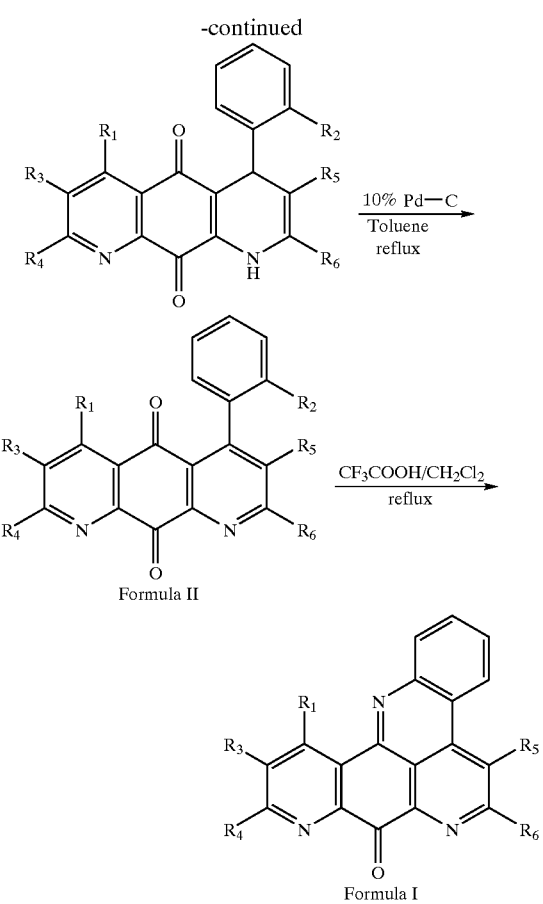

Formula II

Formula I

The examples which follow illustrate the preparation of the compounds of formulae I and II.

EXAMPLE 1

6-Chloro-4-(2-trifluoroacetamidophenyl)pyrido[3,2-g]-quinoline-5,10-dione (CR 8250)

1.2 g (4 mmol) of 4-(2-trifluoroacetamidophenyl)-1-dimethylamino-1-aza-1,3-butadiene and 1 mL of acetic anhydride are added to a solution of 0.7 g (3.63 mmol) of 4-chloroquinoline-5,8-dione in 50 mL of $CH_3CN$. The reaction medium is refluxed for 6 hours and the solvent is evaporated off on a rotary evaporator. After purification by filtration through silica (99.5/0.5 $CH_2Cl_2$/MeOH), 0.46 g of adduct is obtained. This compound is dissolved in 100 mL of toluene, 4 g of Pd/C (10%) are added and the reaction medium is refluxed for 2 hours. After filtering and washing the residue with MeOH and then with $CH_2Cl_2$, the filtrate is concentrated on a rotary evaporator and then purified by flash chromatography on a column of silica (98/2 $CH_2Cl_2$/MeOH) to give 87 mg of compound CRL 8250 in the form of a golden-yellow powder.

Yield: 6%. Melting point: 152° C. $^1$H NMR ($CDCl_3$): 7.21 (d, 1H, J=9 Hz); 7.46 (dd, 1H, J=7.5 and 7.5 Hz); 7.58 (m, 2H); 7.72 (m, 2H); 7.81 (s, 1H); 8.94 (d, 1H, J=5.1 Hz); 9.13 (d, 1H, J=4.7 Hz). $^{13}$C NMR ($CDCl_3$): 115.49 (q, J=287.2 Hz); 125.55; 128.11; 128.27; 129.20; 129.35; 130.16; 131.02; 131.32; 131.52; 133.58; 145.13; 147.57; 148.24; 149.85; 154.35; 154.86; 155.34 (q, J=37 Hz); 179.28; 182.40.

EXAMPLE 2

6-Bromo-4-(2-trifluoroacetamidophenyl)pyrido-[3,2-g]quinoline-5,10-dione

1) Synthesis of 4-Bromo-5,8-dimethoxyquinoline:

3 g (9.35 mmol) of 5,8-dimethoxy-4-quinolyl triflate and 8.2 g (94.2 mmol) of LiBr are added to 60 mL of dioxane and the mixture is refluxed for 30 min. 200 mL of water are then added and the mixture is extracted with ethyl acetate (3 times 200 mL). The organic phases are dried over $MgSO_4$ and the solvent is then evaporated off on a rotary evaporator to give 2.3 g of yellow crystals.

Yield: 91%. Melting point: 86° C. $^1$H NMR ($CDCl_3$): 3.90 (s, 3H); 4.02 (s, 3H); 6.89 (d, 1H, J=8.8 Hz); 6.97 (d, 1H, J=8.8 Hz); 7.71 (d, 1H, J=4.4 Hz); 8.57 (d, 1H, J=4.4 Hz). $^{13}$C NMR ($CDCl_3$): 56.10; 56.26; 107.54; 107.89; 120.49; 128.08; 128.79; 141.81; 148.18; 148.85; 149.44.

2) Synthesis of 4-Bromoquinoline-5,8-dione 100 mg (0.373 mmol) of 4-bromo-5,8-dimethoxyquinoline are dissolved in 8 mL of $CH_3CN$ and 4 mL of water at room temperature. 0.6 g (1.11 mmol) of cerium ammonium nitrate (CAN) is added and the mixture is stirred for 30 min. After evaporating off the $CH_3CN$ on a rotary evaporator, 100 mL of water are added and the medium is extracted with $CHCl_3$ (3 times 100 mL). After drying the organic phases over $MgSO_4$ and evaporating off the solvent on a rotary evaporator, 83 mg of quinone are obtained in the form of a pinkish powder.

Yield: 93%. Melting point: 190° C. $^1$H NMR ($CDCl_3$): 7.06 (d, 1H, J=10 Hz); 7.12 (d, 1H, J=10 Hz); 7.93 (d, 1H, J=5.2 Hz), 8.73 (d, 1H, J=5.2). $^{13}$C NMR ($CDCl_3$): 126.71; 132.83; 134.13; 136.89; 139.16; 148.95; 152.88; 181.53; 182.6. $^{13}$C NMR ($CDCl_3$): 126.71; 132.83; 134.13; 136.89; 139.16; 148.95; 152.88; 181.53; 182.6.

3) Synthesis of 6-Bromo-4-(2-trifluoroacetamidophenyl)-pyrido[3,2-g]quinoline-5,10-dione 3.6 g (12.6 mmol) of 4-(2-trifluoroacetamidophenyl)-1-dimethylamino-1-aza-1,3-butadiene and 5 g of $SiO_2$ are added to a solution of 2 g (8.4 mmol) of 4-bromoquinoline-5,8-dione in 220 mL of $CH_3CN$. The reaction medium is refluxed for 10 hours and the solvent is evaporated off on a rotary evaporator. After purification by flash chromatography on a column of silica (99.5/0.5 $CH_2Cl_2$/MeOH), 0.58 g of adduct is obtained. This compound is dissolved in 21 mL of toluene, 2.1 g of Pd/C (10%) are added and the reaction medium is refluxed for 4 hours. After filtering and washing the residue, the filtrate is concentrated on a rotary evaporator and then purified by flash chromatography on a column of silica (98/2 $CH_2Cl_2$/MeOH) to give 0.19 g of the compound in the form of an orange powder.

Yield: 5%. Melting point: 145° C. $^1$H NMR ($CDCl_3$): 7.21 (dd, 1H, J=7.2 and 1.2 Hz); 7.44 (ddd, 1H, J=7.2 and 7.2 and 1.2 Hz); 7.55 (ddd, 1H, J=7.2 and 7.2 and 1.2 Hz); 7.57 (d, 1H, J=4.8 Hz); 7.69 (dd, 1H, J=7.2 and 1.2 Hz); 7.91 (d, 1H, J=4.8 Hz); 8.20 (broad s, 1H); 8.73 (d, 1H, J=4.8 Hz); 9.05 (d, 1H, J=4.8 Hz). $^{13}$C NMR ($CDCl_3$): 115.12 (q, J=287.1 Hz); 125.41; 127.71; 128.94; 129.30; 129.30; 129.72; 130.91; 131.10; 132.89; 133.31; 134.26; 147.35; 147.79; 149.24; 153.44; 154.30; 154.78 (q, J=36.8 Hz); 178.86; 182.05.

EXAMPLE 3

6-Nitro-4-(2-trifluoroacetamidophenyl)pyrido[3,2-g]-quinoline-5,10-dione

1) Synthesis of 4-Nitro-5,8-dimethoxyquinoline:

1.89 g (8.47 mmol) of 4-chloro-5,8-dimethoxyquinoline, 0.69 g (10.06 mmol) of $NaNO_2$ and 2.9 g (10.59 mmol) of tetrabutylammonium chloride are dissolved in 50 mL of $CH_2Cl_2$ and 50 mL of water. The mixture is left stirring at room temperature for 3 days. The organic phase is recovered and the aqueous phase is extracted 3 times with $CH_2Cl_2$. The organic phases are combined and then dried over $MgSO_4$. After evaporating off the solvent, the residue is fractionated by flash chromatography on a column of silica (98/2 $CH_2Cl_2$/MeOH) and 1.2 g of 4-nitro-5,8-dimethoxyquinoline are obtained in the form of a bright yellow powder.

Yield: 60%. Melting point: 169° C. $^1$H NMR ($CDCl_3$): 3.85 (s, 3H); 4.05 (s, 3H); 6.92 (d, 1H, J=8.8 Hz); 7.07 (d, 1H, J=8.8 Hz); 7.36 (d, 1H, J=4.4 Hz); 9.01 (d, 1H, J=4.4 Hz). $^{13}$C NMR ($CDCl_3$): 56.41; 56.52; 107.61; 108.99; 111.02; 113.69; 141.99; 146.48; 149.31; 149.53; 152.68.

2) Synthesis of 4-Nitroquinoline-5,8-dione 400 mg (1.71 mmol) of 4-nitro-5,8-dimethoxyquinoline are dissolved in 10 mL of $CH_3CN$ and 5 mL of water at room temperature. 2.8 g (5.2 mmol) of cerium ammonium nitrate are added and the reaction medium is stirred for 15 min. After evaporating off the $CH_3CN$ on a rotary evaporator, 10 mL of water are added and the medium is extracted with $CH_2Cl_2$ (3 times 20 mL). After drying the organic phases and evaporating off the solvent on a rotary evaporator, 290 mg of 4-nitroquinoline-5,8-dione are obtained in the form of an orange powder.

Yield: 83%. Melting point: 180° C. $^1$H NMR ($CDCl_3$): 7.10 (d, 1H, J=10.4 Hz); 7.23 (d, 1H, J=10.4 Hz), 7.64 (d, 1H, J=5.6 Hz), 9.24 (d, 1H, J=5.6 Hz). $^{13}$C NMR (DMSO-$d_6$): 118.49; 120.00; 137.89; 139.26; 148.83; 152.83; 156.38; 181.07; 182.04.

3) Synthesis of 6-Nitro-4-(2-trifluoroacetamidophenyl)-pyrido[3,2-g]quinoline-5,10-dione (CRL 8267)

1.5 g (7.35 mmol) of 4-nitroquinoline-5,8-dione, 4.2 g (14.7 mmol) of 4-(2-trifluoroacetamidophenyl)-1-dimethylamino-1-aza-1,3-butadiene and 7.5 mL of acetic anhydride in 100 mL of $CH_3CN$ are refluxed for 18 hours. After evaporating off the solvent on a rotary evaporator and purifying by flash chromatography on a column of silica (95/5 $CH_2Cl_2$/MeOH), 0.8 g of adduct is obtained. This compound is dissolved in 30 mL of toluene, 2.5 g of Pd/C (10%) are added and the mixture is refluxed for 5 hours. After filtering off and washing the residue, the filtrate is concentrated on a rotary evaporator and then purified by flash chromatography on a column of silica (95/5 $CH_2Cl_2$/MeOH) to give 0.4 g of the compound in the form of an beige- colored powder.

Yield: 13%. Melting point: 158° C. $^1$H NMR ($CDCl_3$): 7.34 (d, 1H, J=7.2 Hz); 7.45 (d, 1H, J=7.2 Hz); 7.54 (m, 2H); 7.69 (d, 1H, J=4.4 Hz); 7.77 (d, 1H, J=4.4 Hz); 8.04 (s, 1H); 9.18 (d, 1H, J=4.4 Hz); 9.32 (d, 1H, J=4.4 Hz). $^{13}$C NMR ($CDCl_3$): 115.41 (q, J=287 Hz); 120.85; 122.58; 126.51; 128.16; 129.25; 129.33; 130.39; 130.64; 131.42; 134.24; 148.11; 148.18; 149.11; 154.51; 155.21 (q, 37 Hz); 155.77; 157.13; 177.79; 180.54.

EXAMPLE 4

4-(2-Trifluoroacetamidophenyl)pyrido[3,2-g]quinoline-5,10-dione (CRL 8277)

1 g (6.3 mmol) of quinoline-5,8-dione, 3.59 g (12.6 mmol) of 4-(2-trifluoroacetamidophenyl)-1-dimethylamino-1-aza-1,3-butadiene and 7.5 mL of acetic anhydride in 175 mL of $CH_3CN$ are refluxed for 24 hours. After evaporating off the solvent on a rotary evaporator and purifying by filtration on silica (95/5 $CH_2Cl_2$/MeOH), the adduct is obtained. This compound is dissolved in 150 mL of toluene, 6.2 g of Pd/C (10%) are added and the reaction medium is refluxed for 12 hours. After filtering off and washing the residue with MeOH and then with $CHCl_3$, the filtrate is concentrated on a rotary evaporator and then purified by flash chromatography on a column of silica (95/5 $CH_2Cl_2$/

MeOH) to give 0.125 g of compound CRL 8277 in the form of a yellow powder.

Yield: 5%. Melting point: 205° C. $^1$H NMR (CDCl$_3$): 7.20 (dd, 1H, J=8 and 1.2 Hz); 7.46 (ddd, 1H, J=8 and 1.2 Hz); 7.58 (d, 1H, J=4.4 Hz); 7.59 (ddd, 1H, J=8 and 8 and 1.2 Hz); 7.74 (m, 3H); 8.42 (dd, 1H, J=8 and 1.6 Hz); 9.14 (dd, 1H, 4.4 and 1.6 Hz); 9.16 (d, 1H, J=4.4 Hz). $^{13}$C NMR (CDCl$_3$): 115.46 (q, J=291 Hz); 125.26; 127.45; 127.94; 128.54; 129.01; 129.99; 130.49; 131.15; 131.50; 133.90; 135.57; 147.84; 147.99; 149.68; 154.93; 155.39 (q, J=40 Hz); 155.86; 179.66; 183.19.

EXAMPLE 5

6-Methoxy-4-(2-trifluoroacetamidophenyl)pyrido-[3,2-g]quinoline-5,10-dione (CRL 8275)

3.5 g (16 mmol) of 4-methoxyquinoline-5,8-dione, 7 g (24 mmol) of 4-(2-trifluoroacetamidophenyl)-1-dimethylamino-1-aza-1,3-butadiene and 15 mL of acetic anhydride in 200 mL of CH$_3$CN are refluxed for 18 hours. After evaporating off the solvent on a rotary evaporator and purifying by filtration through silica (99.5/0.5 CH$_2$Cl$_2$/MeOH), 3 g of adduct are obtained. This compound is dissolved in 150 mL of toluene, 6 g of Pd/C (10%) are added and the reaction medium is refluxed overnight. After filtering off and washing the residue with MeOH and then with CHCl$_3$, the filtrate is concentrated on a rotary evaporator and then purified by flash chromatography on a column of silica (95/5 CH$_2$Cl$_2$/MeOH) to give 0.6 g of the compound in the form of a pale green powder.

Yield: 9%. Melting point: 158° C. $^1$H NMR (CDCl$_3$): 4.04 (s, 3H); 7.22 (d, 1H, J=6 Hz); 7.24 (dd, 1H, J=1.6 and 7.6 Hz); 7.46 (dd, 1H, J=7.6 and 7.2 Hz); 7.56 (d, 1H, J=4.8 Hz); 7.60 (dd, 1H, J=7.6 and 7.2 Hz); 7.79 (d, 1H, J=8.4 Hz); 7.97 (s, 1H); 8.95 (d, 1H, J=6 Hz); 9.13 (d, 1H, J=5.2 Hz). $^{13}$C NMR (CDCl$_3$): 65.84; 111.53; 115.34 (q, J=305 Hz); 120.60; 125.44; 127.82; 129.09; 129.46; 129.80; 131.28; 131.70; 133.83; 147.15; 148.22; 150.08; 154.29; 155.09 (q, 42 Hz); 156.07; 165.95; 180.26; 183.00.

EXAMPLE 6

6-(Dimethylamino)-4-(2-trifluoroacetamidophenyl)pyrido-[3,2-g]quinoline-5,10-dione (CRL 8426)

Dimethylamine hydrochloride (0.37 g; 4.6 mmol) and NaOH (0.18 g; 4.6 mmol) are successively added to a solution of the chloro compound CRL 8250 (0.5 g; 1.15 mmol) in water (12 mL) and THF (25 mL). The reaction medium is heated at 60° C. for 3 hours. After concentrating on a rotary evaporator, the crude product obtained is purified by flash chromatography on silica (98/2 CH$_2$Cl$_2$/MeOH) to give, successively, 40 mg of compound CRL 8427 and 70 mg of compound CRL 8426. The compound CRL 8426 is obtained in the form of an orange powder and is characterized by:

Yield: 14%. Melting point: 150° C. IR (KBr): 3175; 1724; 1701; 1654 cm$^{-1}$. MS: m/z 440 (100); 353 (15); 69 (84). $^1$H NMR (CDCl$_3$): 2.75 (s, 6H); 6.94 (d, 1H, J=6 Hz); 7.07 (dd, 1H, J=7.7 and 1.5 Hz); 7.32 (ddd, 1H, J=7.7, 7.7 and 0.7 Hz); 7.49 (d, 1H, J=5 Hz); 7.55 (ddd, 1H, J=7.7, 7.7 and 1.7 Hz); 7.85 (d, 1H, J=7.7 Hz); 8.29 (broad s, 1H); 8.55 (d, 1H, J=6 Hz); 9.05 (d, 1H, J=5 Hz). $^{13}$C NMR (CDCl$_3$): 43.21; 112.58; 115.58 (q, J=287 Hz); 119.13; 125.29; 126.72; 129.03; 129.60; 130.30; 131.13; 132.77; 133.28; 146.18; 147.82; 149.71; 151.05; 153.28; 154.76; 155.76 (q, J=37 Hz); 180.48; 183.96.

EXAMPLE 7

6-(Acetamido)-4-(2-trifluoroacetamidophenyl)pyrido-[3,2-g]quinoline-5,10-dione (CRL 8428)

1) Synthesis of 4-Azido-5,8-dimethoxyquinoline 16.7 g of NaN$_3$ are added to a solution of 10 g (44.7 mmol) of 4-chloro-5,8-dimethoxyquinoline in a DMF/H$_2$O mixture (160 mL/60 mL). The reaction medium is heated at 90° C. for 2 h 30 min. After cooling, the mixture is hydrolyzed with 500 mL of saturated NH$_4$Cl solution and is extracted with CHCl$_3$ (3 times 150 mL) After drying over MgSO4, the organic phases are concentrated on a rotary evaporator and the DMF is then removed under vacuum (2 mmHg). 8.7 g of azide are obtained in the form of a brown powder.

Yield: 85%. Melting point: 106° C. $^1$H NMR (CDCl$_3$): 3.86 (s, 3H); 3.95 (s, 3H); 6.75 (d, 1H, J=8.6 Hz); 6.89 (d, 1H, J=8.6 Hz); 7.10 (d, 1H, J=4.8 Hz); 8.72 (d, 1H, J=4.8 Hz). $^{13}$C NMR (CDCl$_3$): 55.77; 56.50; 106.44; 107.49; 110.76; 114.20; 142.25; 145.45; 148.82; 148.96; 149.13.

2) Synthesis of 4-Amino-5,8-dimethoxyquinoline 12 g (45.8 mmol) of triphenylphosphine are added in a single portion to a solution of 8.7 g (37.8 mmol) of 4-azido-5,8-dimethoxyquinoline in a THF/H$_2$O mixture (110 mL/110 mL). The reaction medium is stirred at ambient temperature for 2 hours and then concentrated on a rotary evaporator. The residue is acidified with 200 mL of 1N HCl and extracted with ether (3 times 500 mL). The aqueous phase is then basified with 250 mL of 1N NaOH and re-extracted with CHCl$_3$ (3 times 250 mL). After drying over MgSO$_4$ and evaporating off the solvent on a rotary evaporator, the expected amine is obtained quantitatively in the form of brown powder, which decomposes before melting.

$^1$H NMR (CDCl$_3$): 3.86 (s, 3H); 3.94 (s, 3H); 5.93 (broad s, 2H); 6.39 (d, 1H, J=5.2 Hz); 6.55 (d, 1H, J=8.8 Hz); 7.77 (d, 1H, J=8.8 Hz); 8.36 (d, 1H, J=5.2 Hz). $^{13}$C NMR (CDCl$_3$): 55.77; 55.80; 102.22; 104.73; 106.32; 111.14; 142.45; 149.48; 149.55; 150.81; 152.09.

3) Synthesis of 4-Acetamido-5,8-dimethoxyquinoline

A suspension of 3 g (14.7 mmol) of 4-amino-5,8-dimethoxyquinoline and of 0.72 g (5.88 mmol) of DMAP in 30 mL of acetic anhydride is stirred at ambient temperature for 24 hours. After concentrating on a rotary evaporator, the reaction medium is washed with 40 mL of saturated NaHCO$_3$ solution and then extracted with CHCl$_3$ (3 times 50 mL). The extracts are dried over MgSO$_4$ and the solvent is evaporated off, followed by evaporation of the remaining acetic anhydride by azeotropic entrainment with benzene. 2.7 g of the expected derivative are obtained in the form of a yellow powder.

Yield: 74%. Melting point: 152° C. $^1$H NMR (CDCl$_3$): 2.26 (s, 3H); 4.03 (s, 6H); 6.81 (d, 1H, J=8.4 Hz); 6.90 (d, 1H, J=8.4 Hz); 8.62 (d, 1H, J=4.8 Hz); 8.78 (d, 1H, J=4.8 Hz); 10.86 (broad s, 1H). $^{13}$C NMR (CDCl$_3$): 14.15; 44.29; 44.91; 93.65; 94.89; 98.22; 99.96; 129.73; 131.69; 137.16; 138.35; 138.57; 157.42.

4) Synthesis of 4-Acetamidoquinoline-5,8-dione 22 g (40.1 mmol) of cerium ammonium nitrate are added, at 0° C., to a solution of 5 g (20.3 mmol) of 4-acetamido-5,8-dimethoxyquinoline in a CH$_3$CN/H$_2$O mixture (50 mL/50 mL). The reaction medium is stirred for 1 h 45 min and is then basified with 500 mL of saturated NaHCO$_3$ solution. 200 mL of H$_2$O are added and the mixture is extracted with CHCl$_3$ (3 times 500 mL) After drying over MgSO$_4$ and evaporating off the solvent, 3.4 g of expected product are obtained in the form of a brown-yellow powder, which is used rapidly for the following step since the product is unstable.

Yield: 77%. $^1$H NMR (CDCl$_3$): 2.28 (s, 3H); 6.97 (d, 1H, J=10.4 Hz); 7.08 (d, 1H, J=10.4 Hz); 8.83 (d, 1H, J=5.6 Hz); 8.88 (d, 1H, J=5.6 Hz); 11.75 (broad s, 1H). $^{13}$C NMR (CDCl$_3$): 26.00; 114.40; 117.75; 138.41; 139.31; 147.34; 148.60; 155.73; 170.53; 182.96; 189.75.

5) Synthesis of 6-(Acetamido)-4-(2-trifluoroacetamidophenyl)pyrido[3,2-g]quinoline-5,10-dione (CRL 8248)

5 g (17.5 mmol) of 4-(2-trifluoroacetamidophenyl)-1-dimethylamino-1-aza-1,3-butadiene, 6 mL of acetic anhydride and 4.4 g of Pd/C (10%) are successively added to a solution of 4-acetamidoquinoline-5,8-dione (3.4 g, 15.7 mmol) in 270 mL of acetonitrile. The reaction medium is refluxed for 15 hours under nitrogen. After evaporating off the solvent on a rotary evaporator, the crude product obtained is purified by flash chromatography on silica (CHCl$_3$ and then 98/2 CHCl$_3$/MeOH) to give a powder which is then washed with hot ether. 80 mg of CRL 8248 are obtained in the form of a brown powder.

Yield: 1%. Melting point: >260° C. IR (CHCl$_3$): 3410; 3277; 1719; 1707; 1702. MS: m/z 454 (9); 412 (7); 343 (100); 300 (17). $^1$H NMR (CDCl$_3$): 2.23 (s, 3H); 7.25 (dd, 1H, J=7.7 and 1.5 Hz); 7.48 (ddd, 1H, J=7.3, 7.7 and 1.1 Hz); 7.53 (dd, 1H, J=4.8 Hz); 7.60 (ddd, 1H, J=7.7, 7.3 and 1.5 Hz); 7.78 (d, 1H, J=7.3 Hz); 7.93 (broad s, 1H); 8.86 (d, 1H, J=5.7 Hz); 8.93 (d, 1H, J=5.7 Hz); 9.08 (d, 1H, J=4.8 Hz). $^{13}$C NMR (CDCl$_3$): 25.20; 115.63 (q, J=288 Hz); 115.93; 116.66; 126.61; 127.86; 128.75; 129.11; 129.28; 131.31; 131.62; 134.87; 146.17; 146.82; 148.33; 149.60; 154.30; 154.82; 154.94 (q, J=36 Hz); 170.13; 179.34; 186.80.

EXAMPLE 8

8-Hydroxy-4-(2-trifluoroacetamidophenyl)pyrido[3,2-g]-quinoline-5,10-dione (CRL 8429)

1.9 g (6.5 mmol) of 4-(2-trifluoroacetamidophenyl)-1-dimethylamino-1-aza-1,3-butadiene, 2.2 mL of acetic anhydride and 1.6 g of Pd/C (10%) are successively added to a solution of 5,8-dioxocarbostyril (1.04 g, 5.9 mmol) in 500 mL of acetonitrile. The reaction medium is refluxed for 15 hours under nitrogen. After evaporating off the solvent on a rotary evaporator, the crude product obtained is purified by flash chromatography on silica (CH$_2$Cl$_2$ and then 95/5 CH$_2$Cl$_2$/MeOH) to give 400 mg of a yellow powder of compound CRL 8249 (or of its oxo tautomer in position 8).

Yield: 16%. Melting point: >260° C. IR(CHCl$_3$): 1664, 1685, 1735, 3334, 3401 cm$^{-1}$. MS: m/z 413 (33); 344 (17); 301 (100); 177 (44). $^1$H NMR (CDCl$_3$): 6.90 (dd, 1H, J=9.9 Hz); 7.19 (dd, 1H, J=7.8 and 1.5 Hz); 7.47 (ddd, 1H, J=7.8, 7.8 and 1.1 Hz); 7.60 (m, 2H); 7.68 (m, 2H); 7.93 (d, 1H, J=9.9 Hz); 9.09 (d, 1H, J=4.8 Hz). $^{13}$C NMR (CDCl$_3$): 115.56 (q, J=288 Hz); 126.34; 126.90; 127.08; 128.69; 129.12; 130.89; 134.61; 135.63; 146.85; 148.02; 150.56; 151.70; 152.83; 154.92; 155.57 (q, J=38 Hz); 161.92; 169.63; 179.50; 181.13.

EXAMPLE 9

8-Methoxy-4-(2-trifluoroacetamidophenyl)pyrido[3,2-g]-quinoline-5,10-dione (CRL 8455)

2 mL (31.8 mmol) of methyl iodide and 500 mg (1.8 mmol) of Ag$_2$CO$_3$ are added to 400 mg (0.97 mmol) of compound CRL 8429 dissolved in 100 mL of CHCl$_3$. The mixture is stirred in the absence of light and at ambient temperature for 60 hours. After evaporating off the solvent, the crude product obtained is purified by flash chromatography (CH$_2$Cl$_2$) to give 52 mg of compound CRL 8455 in the form of a yellow powder.

Yield: 11%. Melting point: >260° C. IR (CHCl$_3$): 1602, 1669, 1701, 1737, 3404 cm$^{-1}$. MS: m/z 427 (17); 426 (30); 357 (14); 315 (74); 314 (100); 286 (7); 177 (23). $^1$H NMR (CDCl$_3$): 4.19 (s, 3H); 7.06 (d, 1H, J=8.8 Hz); 7.20 (dd, 1H, J=7.3 and 1.1 Hz); 7.44 (dd, 1H, J=8.1 and 7.0 Hz); 7.53 (d, 1H, J=5.0 Hz); 7.57 (ddd, 1H, J=7.3, 7.0 and 1.1 Hz); 7.74 (d, 1H, J=8.1 Hz); 7.93 (broad s, 1H); 8.19 (d, 1H, J=8.8 Hz); 9.09 (d, 1H, J=5.0 Hz). $^{13}$C NMR (CDCl$_3$): 55.06; 115.02; 115.56 (q, J=276 Hz); 117.80; 125.22; 125.68; 127.80; 128.95; 129.76; 130.94; 131.58; 134.23; 137.53; 147.47; 147.55; 149.65; 154.30; 155.41 (q, J=38 Hz); 167.73; 179.60; 182.71.

EXAMPLE 10

Ethyl 4-(2-Trifluoroacetamidophenyl)-5,10-dioxopyrido-[3,2-g]quinoline-7-carboxylate (CRL 8454)

1) Synthesis of Ethyl 5,8-Dioxoquinoline-3-carboxylate 7.4 g of cerium ammonium nitrate are added at ambient temperature to a solution of 1 g (3.83 mmol) of ethyl 5,8-dimethoxyquinoline-3-carboxylate in a CH$_3$CN/H$_2$O mixture (45 mL/23 mL). The reaction medium is stirred for 1 hour and the acetonitrile is then evaporated off. The medium is basified by adding 17 mL of saturated NaHCO$_3$ solution. 60 mL of H$_2$O are added and this mixture is then extracted with CH$_2$Cl$_2$ (3 times 100 mL). After drying over MgSO$_4$ and evaporating off the solvent, 0.8 g of ethyl 5,8-dioxoquinoline-3-carboxylate is obtained.

Yield: 91%. Melting point: 124° C. $^1$H NMR (CDCl$_3$): 1.45 (t, 3H; J=7.3 Hz); 4.49 (q, 2H, J=7.3 Hz); 7.13 (d, 1H, J=10.4 Hz); 7.22 (d, 1H, J=10.4 Hz); 8.99 (d, 1H, J=2.2 Hz); 9.58 (d, 1H, J=2.2 Hz). $^{13}$C NMR (CDCl$_3$): 14.22; 62.48; 128.62; 129.86; 135.98; 138.29; 139.33; 149.14; 155.17; 163.44; 182.40; 183.63.

2) Synthesis of Ethyl 4-(2-Trifluoroacetamidophenyl)-5,10-dioxopyrido[3,2-g]quinoline-7-carboxylate (CRL 8454)

0.61 g (2.14 mmol) of 4-(2-trifluoroacetamidophenyl)-1-dimethylamino-1-aza-1,3-butadiene and then 1.4 mL of acetic anhydride are successively added to a solution of ethyl 5,8-dioxoquinoline-3-carboxylate (0.45 g, 1.94 mmol) in 50 mL of acetonitrile. The reaction medium is refluxed for 24 hours under nitrogen. After evaporating off the solvent on a rotary evaporator, the crude product obtained is purified by flash chromatography on silica (CH$_2$Cl$_2$, and then 98/2 CH$_2$Cl$_2$/MeOH) to remove the unreacted starting materials. After concentrating the other fractions obtained, 20 mL of chloroform and 630 mg of MnO$_2$ are added thereto. The mixture is stirred for 3 hours and a second filtration through silica (CH$_2$Cl$_2$) is performed to give the compound CRL 8454 in the form of a brown powder (27 mg).

Yield: 3%. Melting point: 124° C. IR (CHCl$_3$): 1681, 1709, 1730, 3401 cm$^{-1}$. MS: m/z 469 (17); 468 (6); 357 (100); 356 (81); 329 (17); 328 (6). $^1$H NMR (CDCl$_3$): 1.42 (t, 3H, J=7 Hz); 4.45 (q, 2H, J=7 Hz); 7.22 (dd, 1H, J=7.7 and 1.5 Hz); 7.47 (ddd, 1H, J=7.7, 7.7 and 0.8 Hz); 7.61 (ddd, 1H, J=7.7, 7.7 and 1.5 Hz); 7.63 (d, 1H, J=4.8 Hz); 7.68 (broad s, 1H); 7.74 (d, 1H, J=8.1 Hz); 9.00 (d, 1H, J=1.9 Hz); 9.20 (d, 1H, J=4.8 Hz); 9.65 (d, 1H, J=1.9 Hz). $^{13}$C NMR (CDCl$_3$): 14.11; 62.56; 115.46 (q, J=287 Hz); 125.73; 127.50; 127.99; 129.01; 129.97 (2); 130.23; 131.27; 131.43; 134.16; 136.91 (2); 148.32; 149.53; 154.88; 155.57 (q, J=38 Hz); 155.76; 163.11; 179.05; 182.10.

EXAMPLE 11

6-Chloro-4-(2-nitrophenyl)pyrido[3,2-g]quinoline-5,10-dione (CRL 8296)

This compound was synthesized according to the process described by Kitahara et al., Tetrahedron, 1998, 54, 8421–8432.

EXAMPLE 12

6-Methoxy-4-(2-nitrophenyl)pyrido[3,2-g]quinoline-5,10-dione (CRL 8243)

This compound was synthesized according to the process described by Kitahara et al., Tetrahedron, 1998, 54, 8421–8432.

EXAMPLE 13

6-Amino-4-(2-nitrophenyl)pyrido[3,2-g]quinoline-5,10-dione (CRL 8300)

This compound was synthesized according to the process described by Kitahara et al., Tetrahedron, 1998, 54, 8421–8432.

EXAMPLE 14

8-Hydroxy-4-(2-nitrophenyl)pyrido[3,2-g]quinoline-5,10-dione (CRL 8456)

2.06 g (9.42 mmol) of 4-(2-nitrophenyl)-1-dimethylamino-1-aza-1,3-butadiene and 8.2 mL of acetic anhydride are successively added to a solution of 5,8-dioxocarbostyril (1.5 g, 8.56 mmol) in 300 mL of acetonitrile. The reaction medium is refluxed for 85 hours under nitrogen. After evaporating off the solvent on a rotary evaporator, the crude product obtained is purified by flash chromatography on silica ($CH_2Cl_2$ and then 99/1 $CH_2Cl_2$/MeOH) to give 205 mg of a yellow powder of the compound CRL 8456 (or of its oxo tautomer in position 8).

Yield: 7%. Melting point: >260° C. IR ($CHCl_3$): 1666, 1687 cm$^{-1}$. MS: m/z 301 (100; M-$NO_2$); 273 (21); 261 (25). $^1$H NMR (DMSO-$d_6$): 6.71 (d, 1H, J=9.0 Hz); 7.35 (d, 1H, J=7.7 Hz); 7.70 (d, 1H, J=5.0 Hz); 7.74 (ddd, 1H, J=7.7; 6.6 and 0.9 Hz); 7.81 (d, 1H, J=9.0 Hz); 7.85 (ddd, 1H, J=7.7; 6.6 and 0.9 Hz); 8.29 (d, 1H, J=7.7 Hz); 9.06 (d, 1H, J=5.0 Hz). $^{13}$C NMR (DMSO-$d_6$) 114.02; 114.46; 122.55; 124.12; 125.79; 129.12; 129.82; 130.23; 134.13; 135.53; 146.44; 147.80; 148.05; 153.20; 165.33; 175.50; 180.30 (1 C not observed).

EXAMPLE 15

8-Methoxy-4-(2-nitrophenyl)pyrido[3,2-g]quinoline-5,10-dione (CRL 8457)

1.2 mL (19.27 mmol) of methyl iodide and 158 mg (1.8 mmol) of $Ag_2CO_3$ are added to 100 mg (0.288 mmol) of the compound CRL 8456 dissolved in 75 mL of $CHCl_3$. The mixture is stirred in the absence of light at 50° C. for 48 hours. After evaporating off the solvent, the crude product obtained is purified by flash chromatography ($CH_2Cl_2$) to give 56 mg of the compound CRL 8457 in the form of a yellow powder.

Yield: 54%. Melting point: >260° C. IR ($CHCl_3$): 1670, 1701 cm$^{-1}$. MS: m/z 361 (2); 315 (42); 314 (100); 286 (32); 257 (7); 188 (15). $^1$H NMR ($CDCl_3$): 4.21 (s, 3H); 7.06 (d, 1H, J=8.8 Hz); 7.27 (dd, 1H, J=7.5 and 1.5 Hz); 7.45 (d, 1H, J=4.8 Hz); 7.69 (ddd, 1H, J=1.5; 8.2 and 7.5 Hz); 7.77 (ddd, 1H, J=7.5; 8.2 and 1.1 Hz); 8.20 (d, 1H, J=8.4 Hz); 8.34 (dd, 1H, J=8.2 and 1.1 Hz); 9.14 (d, 1H, J=4.8 Hz). $^{13}$C NMR ($CDCl_3$): 55.00; 117.62; 124.77; 125.53; 126.64; 128.51; 129.40; 129.85; 133.93; 135.03; 137.64; 146.82; 147.68; 149.25; 149.43; 154.24; 167.63; 179.85; 182.07.

EXAMPLE 16

Ethyl 4-(2-Nitrophenyl)-5,10-dioxopyrido[3,2-g]-quinoline-7-carboxylate (CRL 8453)

0.33 g (1.47 mmol) of 4-(2-nitrophenyl)-1-dimethylamino-1-aza-1,3-butadiene and 1.4 mL of acetic anhydride are successively added to a solution of ethyl 5,8-dioxoquinoline-3-carboxylate (0.3 g, 1.29 mmol) in 50 mL of acetonitrile. The reaction medium is refluxed for 64 hours under nitrogen. After evaporating off the solvent on a rotary evaporator, the crude product obtained is purified by flash chromatography on silica ($CH_2Cl_2$ and then 98/2 $CH_2Cl_2$/MeOH) to give the compound CRL 8453 in the form of a brown powder (53 mg).

Yield: 10%. Melting point: the product decomposes. IR ($CHCl_3$): 1680, 1706, 1728 cm$^{-1}$. MS: m/z 357 (100); 356 (85); 329 (17); 328 (8). $^1$H NMR ($CDCl_3$): 1.41 (t, 3H, J=7 Hz); 4.44 (q, 2H, J=7 Hz); 7.28 (dd, 1H, J=7.7 and 1.5 Hz); 7.54 (d, 1H, J=4.8 Hz); 7.72 (dd, 1H, J=8.0 and 1.5 Hz); 7.80 (ddd, 1H, J=7.7, 8.0 and 1.5 Hz); 8.37 (dd, 1H, J=8.0 and 1.5 Hz); 8.97 (d, 1H, J=2 Hz); 9.21 (d, 1H, J=4.8 Hz); 9.65 (d, 1H, J=2 Hz). $^{13}$C NMR ($CDCl_3$): 14.19; 62.49; 124.91; 127.08; 128.93; 129.74; 129.78; 129.82; 130.23; 134.13; 134.45; 137.05; 146.80; 149.40; 149.85; 149.88; 155.11; 155.99; 163.26; 179.28; 181.96.

EXAMPLE 17

12-Chlorobenzo[b]pyrido[4,3,2-de][1,7]phenanthroline-8-one (CRL 8242)

A suspension of 100 mg (0.274 mmol) of the compound of Example 11 and 200 mg (10 equivalents) of zinc powder in 3 mL of glacial acetic acid is stirred at ambient temperature for 2 h 30 min. The reaction medium is poured into 50 mL of saturated $NaHCO_3$ solution containing 4 g of CAN; the mixture is stirred for 5 min and then extracted with $CHCl_3$ (3 times 50 mL). After drying the organic phases over $MgSO_4$ and evaporating off the solvent on a rotary evaporator, the residue obtained is chromatographed on a column of silica (97/3 $CH_2Cl_2$/MeOH) to give 83 mg of compound in the form of yellow crystals.

Yield: 95%. Melting point: >260° C. $^1$H NMR ($CDCl_3$): 7.77 (d, 1H, J=4.8 Hz); 7.80 (dd, 1H, J=8 and 8 Hz); 7.89 (dd, 1H, J=8 and 8 Hz); 8.25 (d, 1H, J=8 Hz); 8.51 (d, 1H, J=8 Hz); 8.61 (d, 1H, J=5.6 Hz); 8.84 (d, 1H, J=4.8 Hz); 9.28 (d, 1H, J=5.6 Hz). $^{13}$C NMR ($CDCl_3$): 118.06; 120.19; 129.79; 122.65; 129.42; 129.95; 131.66; 131.77; 132.01; 137.88; 144.71; 145.78; 147.01; 149.77; 150.27; 151.22; 176.83; 179.88.

EXAMPLE 18

12-Nitrobenzo[b]pyrido[4,3,2-de][1,7]phenanthroline-8-one (CRL 8273)

365 mg (0.826 mmol) of the compound of Example 3 and 2 mL of trifluoroacetic acid in 20 mL of $CH_2Cl_2$ are refluxed for 3 hours. After evaporating off the solvent on a rotary evaporator, the residue is taken up in 20 mL of 1N NaOH and 20 mL of $CHCl_3$ and the reaction medium is stirred overnight. The organic phase is recovered and the aqueous phase is extracted with $CHCl_3$ (5 times 20 mL). After drying the organic phases over $MgSO_4$ and evaporating off the solvent on a rotary evaporator, the residue is purified by flash chromatography on a column of RP8 grafted silica (60/40 MeOH/$H_2O$) to give 135 mg of compound in the form of pale orange-yellow crystals.

Yield: 50%. Melting point: >260° C. $^1$H NMR ($CDCl_3$): 7.26 (d, 1H, J=5.6 Hz); 7.87 (ddd, 1H, J=8.4 and 8.4 and 1.2 Hz); 7.97 (ddd, 1H, J=8.4 and 8.4 and 1.2 Hz); 8.23 (dd, 1H, J=8.4 and 1.2 Hz); 8.64 (dd, 1H, J=8.4 and 1.2 Hz); 8.67 (d, 1H, J=5.6 Hz); 8.79 (d, 1H, J=5.6 Hz); 9.39 (d, 1H, J=5.6 Hz). $^{13}$C NMR ($CDCl_3$): 116.47; 116.96; 117.65; 119.76;

121.70; 123.32; 129.31; 129.63; 132.56; 137.88; 142.46; 147.52; 148.85; 151.53; 152.11; 153.68; 167.23; 180.33.

EXAMPLE 19

Benzo[b]pyrido[4,3,2-de][1,7]phenanthroline-8-one (CRL 8299)

30 mg (0.0756 mmol) of the compound of Example 4 and 1 mL of trifluoroacetic acid in 2 mL of $CH_2Cl_2$ are refluxed for 3 hours. After evaporating off the solvent on a rotary evaporator, the residue is taken up in 2 mL of 1N NaOH and 2 mL of $CHCl_3$ and the mixture is stirred overnight. After recovering the organic phase, the aqueous phase is extracted with $CHCl_3$ (5 times 10 mL). After drying the organic phases over $MgSO_4$ and evaporating off the solvent on a rotary evaporator, 17 mg of compound are obtained in the form of yellow-colored crystals.

Yield: 80%. Melting point: >260° C. $^1H$ NMR ($CDCl_3$): 7.94 (dd, 1H, J=4.4 and 8 Hz); 7.97 (dd, 1H, J=8.2 and 8.2 Hz); 8.10 (dd, 1H, J=8.2 and 8.2 Hz); 8.48 (d, 1H, J=8.2 Hz); 8.76 (d, 1H, J=8.2 Hz); 8.80 (d, 1H, J=5.2 Hz); 9.23 (dd, 1H, J=1.6 and 4.4 Hz); 9.49 (d, 1H, J=5.2 Hz); 9.50 (dd, 1H, J=1.6 and 8 Hz). $^{13}C$ NMR ($CDCl_3$): 118.06; 119.82; 121.88; 123.02; 128.07; 129.33; 131.44; 131.98; 132.98; 134.17; 138.08; 145.62; 147.27; 147.50; 147.76; 150.46; 153.18; 180.94.

EXAMPLE 20

12-Methoxybenzo[b]pyrido[4,3,2-de][1,7]phenanthroline-8-one (CRL 8276)

This compound was synthesized according to the process described by Kitahara et al., Tetrahedron, 1998, 54, 8421–8432.

EXAMPLE 21

12-Bromobenzo[b]pyrido[4,3,2-de][1,7]phenanthroline-8-one Trifluoroacetate (CRL 8259)

200 mg (0.42 mmol) of the compound of Example 2 and 3 drops of trifluoroacetic acid in 50 mL of $CH_2Cl_2$ are refluxed for 30 min. After evaporating off the solvent on a rotary evaporator, the residue is purified by flash chromatography on RP8 grafted silica (50/50 MeOH/$H_2O$) to give 130 mg of compound CRL 8259 in the form of orange-colored crystals.

Yield: 65%. $^1H$ NMR (DMSO-$d_6$): 6.66 (m, 1H); 7.35 (d, 1H, J=7.2 Hz); 7.43 (m, 2H); 7.51 (d, 1H, J=8 Hz); 7.54 (d, 1H, J=5.2 Hz); 7.97 (m, 1H); 8.99 (d, 1H, J=5.2 Hz); 10.9 (s, 1H). $^{13}C$ NMR (DMSO-$d_6$): 115.66 (q, J=287.1 Hz); 118.30; 124.28; 126.48; 127.36; 128.53; 128.71; 129.31; 131.38; 131.49; 135.91; 147.11; 147.40; 152.83; 154.88 (q, J=36.6 Hz); 178.87 (4 C are not observed).

EXAMPLE 22

12-Nitrobenzo[b]pyrido[4,3,2-de][1,7]phenanthroline-8-one Trifluoroacetate (CRL 8258)

150 mg (0.34 mmol) of the compound of Example 3 and 8 drops of trifluoroacetic acid are dissolved in 10 mL of $CH_2Cl_2$ and the mixture is refluxed for 3 hours. After evaporating off the solvent on a rotary evaporator, the residue obtained is purified by flash chromatography on RP8 grafted silica (60/40 MeOH/$H_2O$) to give 123 mg of compound CRL 8258 in the form of dark orange-yellow crystals.

Yield: 82%. Melting point: >260° C. $^1H$ NMR (DMSO-$d_6$): 6.65 (m, 1H); 7.47 (d, 1H, J=8 Hz); 7.20 (m, 2H); 7.54 (d, 1H, J=8 Hz); 7.57 (d, 1H, J=4.8 Hz); 8.00 (m, 1H); 9.02 (d, 1H, J=4.8 Hz); 10.90 (s, 1H). $^{13}C$ NMR (DMSO-$d_6$): 115.66 (q, J=287 Hz); 118.27; 122.18; 122.24; 126.48; 127.36; 128.53; 128.71; 129.31; 131.40; 131.47; 135.91; 147.13; 147.38; 152.85; 154.88 (q, J=36.6 Hz); 178.85; (3 C are not observed).

EXAMPLE 23

12-Dimethylaminobenzo[b]pyrido[4,3,2-de][1,7]phenanthroline-8-one (CRL 8427)

40 mg of CRL 8427 were obtained in the form of a red powder according to the process described in Example 6.

Yield: 11%. Melting point: 238° C. IR (KBr): 1690 $cm^{-1}$. MS: m/z 326 (44); 311 (100); 254 (14). $^1H$ NMR ($CDCl_3$): 3.10 (s, 6H); 7.10 (d, 1H, J=5.5 Hz); 7.73 (dd, 1H, J=6.8 and 6.8 Hz); 7.87 (dd, 1H, J=6.8 and 6.8 Hz); 8.22 (d, 1H, J=6.8 Hz); 8.54 (m, 2H); 8.59 (d, 1H, 5.5 Hz); 9.26 (d, 1H, J=5.2 Hz). $^{13}C$ NMR ($CDCl_3$): 44.07; 113.72; 117.93; 119.68; 120.41; 122.89; 128.44; 130.47; 131.74; 137.82; 145.29; 146.53; 149.38; 150.06; 150.32; 151.18; 156.85; 181.72 (1 C not observed).

EXAMPLE 24

10-Hydroxybenzo[b]pyrido[4,3,2-de][1,7]phenanthroline-8-one (CRL 8432)

22 mL of 1N NaOH are added to 180 mg (0.44 mmol) of compound CRL 8429 (Example 8) dissolved in 70 mL of $CHCl_3$. The reaction medium is stirred overnight. After neutralization with acetic acid, the organic phase is recovered and the aqueous phase is extracted with a 95/5 $CHCl_3$/MeOH mixture (3 times 50 mL). After drying over $MgSO_4$ and concentrating on a rotary evaporator, 110 mg of a purple powder of compound CRL 8432 (or of its exo tautomer in position 10) are obtained.

Yield: 85%. Melting point: >260° C. IR (KBr): 1664, 1608 $cm^{-1}$. MS: m/z 229 (100); 298 (66); 271 (17); 270 (13); 243 (39); 242 (29). $^1H$ NMR (DMSO-$d_6$): 6.91 (d, 1H, J=9.2 Hz); 7.84 (d, 1H, J=7.8 and 8.8 Hz); 7.97 (dd, 1H, J=7.8 and 7.8 Hz); 8.21 (d, 1H, J=7.8 Hz); 8.71 (d, 1H, J=9.2 Hz); 8.87 (d, 1H, J=8.8 Hz); 9.04 (d, 1H, J=5.5 Hz); 9.27 (d, 1H, J=5.5 Hz).

EXAMPLE 25

10-Methoxybenzo[b]pyrido[4,3,2-de][1,7]phenanthroline-8-one (CRL 8452)

A mixture of the compound CRL 8457 (Example 15–52 mg, 0.14 mmol) and Pd/C (10%, 50 mg) in 30 mL of methanol are hydrogenated at atmospheric pressure. The reaction medium is maintained under a hydrogen atmosphere for 30 minutes. After evaporating off the solvent, the crude product obtained is purified by flash chromatography on silica ($CH_2Cl_2$) to give the compound CRL 8452 in the form of a yellow powder (10 mg).

Yield: 22%. Melting point: >260° C. IR($CDCl_3$): 1684 $cm^{-1}$. MS: m/z 313 (35); 312 (100); 283 (52); 282 (98); 254 (22). $^1H$ NMR ($CDCl_3$): 4.22 (s, 3H); 7.20 (d, 1H, J=8.8 Hz); 7.75 (ddd, 1H, J=8.1; 8.1 and 1.1 Hz); 7.88 (ddd, 1H, J=8.1; 8.1 and 1.1 Hz); 8.24 (d, 1H, J=8.1 Hz); 8.54 (d, 1H, J=8.1 Hz); 8.58 (d, 1H, J=5.5 Hz); 9.13 (d, 1H, J=8.8 Hz); 9.29 (d, 1H, J=5.5 Hz). $^{13}C$ NMR ($CDCl_3$): 52.77; 116.70; 117.05; 118.95; 120.91; 122.27; 127.21; 128.08; 130.52; 131.12;

135.99; 137.19; 145.09; 145.48; 146.81; 147.38; 149.62; 165.29; 180.04.

EXAMPLE 26

Ethyl 8-Oxobenzo[b]pyrido[4,3-de][1,7] phenanthroline-11-carboxylate (CRL 8447)

A mixture of compound CRL 8453 (60 mg, 0.15 mmol) and of Pd/C (10%, 48 mg) in 10 mL of methanol are hydrogenated at atmospheric pressure. The reaction medium is maintained under a hydrogen atmosphere for 2 hours. After evaporating off the solvent, the crude product obtained is purified by flash chromatography on silica (98/2 $CH_2Cl_2$/MeOH) to give the expected compound CRL 8447 in the form of a yellow powder (33 mg).

Yield: 63%. Melting point: >260° C. IR(CHCl$_3$): 1693, 1726 cm$^{-1}$. MS: m/z 355 (100). $^1$H NMR (CDCl$_3$): 1.53 (t, 3H, J=7.3 Hz); 4.57 (q, 2H, J=7.3 Hz); 7.86 (ddd, 1H, J=8.0, 8.0 and 1.1 Hz); 7.99 (ddd, 1H, J=8.0, 8.4 and 1.1 Hz); 8.42 (d, 1H, J=8.4 Hz); 8.64 (d, 1H, J=8.0 Hz); 8.70 (d, 1H, J=5.5 Hz); 9.37 (d, 1H, J=5.5 Hz); 9.59 (d, 1H, J=2.2 Hz); 9.90 (d, 1H, 2.2 Hz). $^{13}$C NMR (CDCl$_3$): 13.01; 60.97; 116.85; 118.69; 120.56; 121.68; 128.30; 128.49; 130.31; 130.79; 131.29; 134.52; 136.82; 144.27; 145.31; 145.83; 148.13; 149.29; 151.91; 162.90; 178.99.

The results of the pharmacological tests, presented below, demonstrate the cytotoxic properties of the compounds of formulae I and II, and also the maximum tolerated doses.

1—Determination of the Maximum Tolerated Dose (MTD)

The evaluation of the maximum tolerated dose was carried out on 4- to 6-week-old B6D2F1/Jico mice. The compounds were administered intraperitoneally at increasing doses ranging from 2.5 to 160 mg/kg. The value of the MTD (expressed in mg/kg) is determined from observing the survival rate of the animals over a period of 14 days after a single administration of the product under consideration. The change in the weight of the animals is also monitored over this period.

The results of the estimation of the maximum tolerated dose (MTD) are collated in table I below:

TABLE I

| CRL compounds | MTD (mg/kg) |
| --- | --- |
| CRL 8348 (Meridine) | >160 |
| Cystodamine | >160 |
| CRL 8276 (Example 20) | 80 |
| CRL 8299 (Example 19) | 80 |
| CRL 8243 (Example 12) | >160 |
| CRL 8296 (Example 11) | 80 |
| CRL 8300 (Example 13) | 80 |
| CRL 8275 (Example 5) | 80 |
| CRL 8277 (Example 4) | >40 |
| CRL 8242 (Example 17) | >160 |
| CRL 8250 (Example 1) | 20 |
| CRL 8258 (Example 22) | 40 |
| CRL 8273 (Example 18) | >80 |
| CRL 8259 (Example 21) | 40 |
| CRL 8267 (Example 3) | 20 |
| CRL 8426 (Example 6) | >160 |
| CRL 8428 (Example 7) | >160 |
| CRL 8427 (Example 23) | >160 |
| CRL 8429 (Example 8) | 40 |
| CRL 8432 (Example 24) | >160 |

2—Cytotoxic Activity on Tumor Cell Lines in Culture

The influence of the compounds of formulae I and II on neoplastic cells was evaluated using the MTT calorimetric test. The principle of the MTT test is based on the mitochondrial reduction by metabolically active live cells of the yellow-colored product MTT (3-(4,5-dimethylthiazol-2-yl)-2,5-diphenyltetrazolium bromide) to a blue-colored product, formazan. The amount of formazan thus obtained is directly proportional to the amount of live cells present in the culture well(s). This amount of formazan is measured by spectrophotometry.

The cell lines are maintained in monolayer culture at 37° C. in stoppered culture dishes containing 25 MM HEPES MEM (Minimum Essential Medium) base medium. This medium, which is suitable for growing a range of varied diploid or primary mammalian cells, is then supplemented:

- with a an amount of 5% FCS (Fetal Calf Serum) decomplemented at 56° C. for 1 hour,
- with 0.6 mg/mL of L-glutamine,
- with 200 IU/mL of penicillin,
- with 200 mg/mL of streptomycin,
- with 0.1 mg/mL of gentamicin.

The 12 human cancer cell lines used were obtained from the *American Type Culture Collection* (ATCC, Rockville, Md., USA). These 12 cell lines are:

- U-373MG (code ATCC: HTB-17) and U-87MG (code ATCC: HTB-14) which are two glioblastomas,
- SW1088 (code ATCC: HTB-12) which is an astrocytoma,
- A549 (code ATCC: CCL-185) and A-427 (code ATCC: HTB-53) which are two non-small-cell lung cancers,
- HCT-15 (code ATCC: CCL-225) and LoVo (code ATCC: CCL-229) which are two colorectal cancers,
- T-47D (code ATCC: HTB-133) and MCF7 (code ATCC: HTB-22) which are two breast cancers,
- J82 (code ATCC: HTB-1) and T24 (code ATCC: HTB-4) which are two bladder cancers,
- PC-3 (code ATCC: CRL-1435) which is a prostate cancer.

Experimentally: 100 µl of a cell suspension containing 200 000 to 50 000 (depending on the cell type used) cells/mL of culture medium are inoculated in flat-bottomed 96-well multi-well plates and are incubated at 37° C. under an atmosphere comprising 5% $CO_2$ and 70% humidity. After incubating for 24 hours, the culture medium is replaced with 100 µl of fresh medium containing either the various test compounds at concentrations ranging from $10^{-5}$ to $10^{-10}$ M or the solvent used to dissolve the test products (control condition). After incubating for 72 hours under the above conditions, the culture medium is replaced with 100 µl of a yellowish solution of MTT dissolved at a rate of 1 mg/mL in RPMI 1640. The microplates are reincubated for 3 hours at 37° C. and then centrifuged for 10 minutes at 400×g. The yellowish solution of MTT is removed and the blue formazan crystals formed at the cellular level are dissolved in 100 µl of DMSO. The microplates are then agitated for 5 minutes. The intensity of the resulting blue coloration, and thus of the conversion of the yellow MTT product into blue formazan by the cells that are still alive at the end of the experiment is quantified by spectrophotometry using a DYNATECH IMMUNOASSAY SYSTEM machine at wavelengths of 570 nm and 630 nm corresponding, respectively, to the maximum absorption wavelengths of formazan and to the background noise. Software built into the spectrophotometer calculates the average optical density values and also the standard deviation (Std. Dev.) and standard error of mean (SEM) values.

The inhibitory activity on the cell growth of the compounds of formula I and of formula II on the different tumor cell lines was compared with that of the natural product meridine (CRL 8348). All of the compounds of formula I and of formula II show significant inhibitory activity on the cell proliferation of the 12 human tumor lines: U-87MG, U-373MG, SW 1088, T24, J82, HCT-15, LoVo, MCF7, T-47D, A549, A-427 and PC-3 with an inhibitory concentration 50 ($IC_{50}$) which is between $10^{-6}$ M and $10^{-10}$M, depending on the compounds and the tumor lines tested. By way of example, the values of the concentrations flanking the $IC_{50}$ which are obtained on the various cell lines are given in table II:

TABLE II

| | COMPOUNDS (Concentration M) | | | | |
|---|---|---|---|---|---|
| CELL LINES | CRL8348 (meridine) | CRL8276 | CRL8299 | CRL8275 | CRL8277 |
| U-87MG | $[10^{-6},10^{-7}]$ | $<10^{-10}$ | $<10^{-10}$ | $<10^{-10}$ | $[10^{-9},10^{-10}]$ |
| U-373MG | $10^{-7}$ | $<10^{-10}$ | $[10^{-9},10^{-10}]$ | $<10^{-10}$ | $[10^{-8},10^{-9}]$ |
| SW1088 | $[10^{-5},10^{-6}]$ | $[10^{-7},10^{-8}]$ | $[10^{-7},10^{-8}]$ | $[10^{-7},10^{-8}]$ | $[10^{-7},10^{-8}]$ |
| T24 | $[10^{-7},10^{-8}]$ | $[10^{-8},10^{-9}]$ | $<10^{-10}$ | $[10^{-8},10^{-9}]$ | $[10^{-7},10^{-8}]$ |
| J82 | $[10^{-5},10^{-6}]$ | $[10^{-9},10^{-10}]$ | $[10^{-8},10^{-9}]$ | $[10^{-9},10^{-10}]$ | $[10^{-7},10^{-8}]$ |
| HCT-15 | $[10^{-6},10^{-7}]$ | $[10^{-8},10^{-9}]$ | $[10^{-8},10^{-9}]$ | $[10^{-8},10^{-9}]$ | $[10^{-8},10^{-9}]$ |
| LoVo | $[10^{-7},10^{-8}]$ | $[10^{-9},10^{-10}]$ | $[10^{-7},10^{-8}]$ | $[10^{-9},10^{-10}]$ | $[10^{-8},10^{-9}]$ |
| MCF7 | $[10^{-7},10^{-8}]$ | $<10^{-10}$ | $[10^{-9},10^{-10}]$ | $[10^{-9},10^{-10}]$ | $[10^{-8},10^{-9}]$ |
| T-47D | $[10^{-7},10^{-8}]$ | $[10^{-7},10^{-8}]$ | $10^{-8}$ | $[10^{-7},10^{-8}]$ | $[10^{-7},10^{-8}]$ |
| A549 | $[10^{-7},10^{-8}]$ | $[10^{-9},10^{-10}]$ | $[10^{-7},10^{-8}]$ | $<10^{-10}$ | $[10^{-8},10^{-9}]$ |
| A-427 | $[10^{-6},10^{-7}]$ | $[10^{-8},10^{-9}]$ | $[10^{-9},10^{-10}]$ | $[10^{-8},10^{-9}]$ | $[10^{-7},10^{-8}]$ |
| PC-3 | $[10^{-6},10^{-7}]$ | $[10^{-7},10^{-8}]$ | $[10^{-7},10^{-8}]$ | $[10^{-7},10^{-8}]$ | $[10^{-7},10^{-8}]$ |

Table III gives the results of the average $IC_{50}$ values (in nM) (calculated from the cytotoxic activity on the 12 tumor lines studied) and the $MTD/IC_{50}$ ratios (these ratios are calculated by forming the ratio of the MTD values and the $IC_{50}$ values expressed as numbers without units).

TABLE III

| CRL compounds | $IC_{50}$(nM) | $MTD/IC_{50}$ | $MTD/IC_{50}$* |
|---|---|---|---|
| CRL 8348 (Meridine) | 170 | 0.94 | 1 |
| Cystodamine | 100 | 1.6 | 1.7 |
| CRL 8276 (Example 20) | 2.1 | 38.1 | 40.5 |
| CRL 8299 (Example 19) | 2.2 | 36.4 | 38.7 |
| CRL 8275 (Example 5) | 2.3 | 34.8 | 37 |
| CRL 8277 (Example 4) | 12.5 | 6.4 | 6.8 |

*: the ratio $MTD/IC_{50}$ for the various compounds was estimated taking as reference a ratio equal to 1 for meridine.

The compounds described show, on the tumor cell line models, $IC_{50}$ values (nM) which are less than or equivalent to those of the natural compounds (meridine and cystodamine). Their maximum tolerated doses are close to those of meridine and cystodamine. When their $IC_{50}$ value is markedly less than that of the natural products, the tolerance/cytotoxic activity ratios for the compounds illustrated in the present invention then become markedly greater than that of meridine and cystodamine, as indicated in Table III. These compounds may thus be used as antitumor medicinal products, for their cytotoxic properties, at tissue concentrations that are higher than those induced with the natural products meridine and cystodamine. They are thus characterized by better therapeutic manageability.

By virtue of their cytotoxic properties, the compounds of formulae I and II as described, or in the form of acceptable pharmaceutical salts or solvates, may be used as active principles of medicinal products.

The compounds of formulae I and II are generally administered in dosage units established either per m² of body surface or per kg of weight. The said dosage units are preferably formulated in pharmaceutical compositions in which the active principle is mixed with one (or more) pharmaceutical excipient(s).

The compounds of formulae I and II above may be used, according to the cancer pathology of the individual to be treated, at doses of between 0.05 and 350 mg/m² of body surface, preferably at doses from 0.5 to 50 mg/m²/day for a curative treatment in the acute phase as a function of the number of treatment cycles of each cure. For maintenance treatment, the compounds of formulae I and II will advantageously be used at doses from 0.05 to 25 mg/m²/day and preferably at doses from 0.1 to 1.5 mg/m²/day depending on the number of treatment cycles of the cure.

In the pharmaceutical compositions of the present invention for oral or intravenous administration, the active principles may be administered in unit forms of administration, mixed with conventional pharmaceutical supports that are suitable for human therapy. The suitable unit forms of administration comprise oral-route forms such as tablets, which may be splittable, or gel capsules, implants and intravenous administration forms.

For a parenteral administration (intravenous infusion at a constant flow rate), sterile aqueous suspensions, sterile isotonic saline solutions or sterile and injectable solutions which contain pharmacologically compatible dispersants and/or solubilizing agents, for example propylene glycol or polyethylene glycol, are used.

Thus, to prepare an aqueous solution for intravenous injection intended for an infusion performed over 1 to 24 h, it is possible to use a co-solvent: an alcohol such as ethanol, a glycol such as polyethylene glycol or propylene glycol, and a hydrophilic surfactant such as Tween® 80.

When a solid composition in the form of tablets is prepared, a wetting agent such as sodium lauryl sulfate may be added to the micronized or unmicronized active principle, and the whole is mixed with a pharmaceutical vehicle such as silica, gelatin, starch, lactose, magnesium stearate, talc, gum arabic or the like. The tablets may be coated with sucrose, with various polymers or with other suitable materials, or alternatively they may be treated such that they have sustained or delayed activity and such that they continuously release a predetermined amount of active principle.

A preparation as gel capsules is obtained by mixing the active principle with a diluent such as a glycol or a glycerol ester and by incorporating the mixture obtained into soft or hard gel capsules.

The active principle may also be formulated in the form of microcapsules or microspheres, optionally with one or more supports or additives.

The active principle may also be presented in the form of a complex with a cyclodextrin, for example α-, β- or γ-cyclodextrin, 2-hydroxypropyl-β-cyclodextrin or methyl-β-cyclodextrin.

The compounds of formulae I and II will be used in the treatment of most solid tumors on account of their powerful cytotoxic activities, in particular for treating cerebral tumors, lung cancers, ovarian and breast tumors, colorectal cancers, prostate cancers and testicular tumors.

What is claimed is:

1. A pharmaceutical composition comprising an effective amount of a compound chosen from the compounds of formulae:

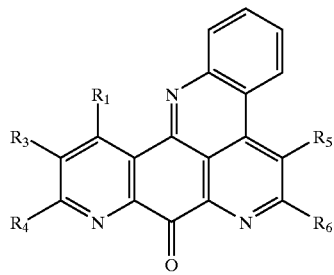

Formula I

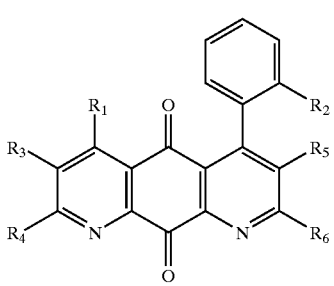

Formula II in which:

$R_1$, $R_3$, $R_4$, $R_5$ and $R_6$ are chosen from hydrogen, halogens and hydroxyl, —CHO, —OR, —COOH, —CN, —CO$_2$R, —CONHR, —CONRR',

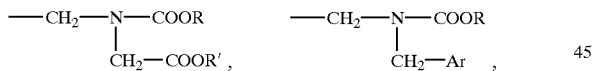

—NH$_2$, —NHR, —N(R)$_2$, —NH—CH$_2$—CH$_2$—N(CH$_3$)$_2$, —NHCOR, morpholino, nitro and —SO$_3$H groups, R and R' being chosen from $C_1$–$C_6$ alkyl groups and Ar being a $C_6$–$C_{14}$ aryl group, $R_2$ is chosen from nitro and —NHCOCF$_3$ groups, with the exclusion of the compounds of formula I in which $R_1$=—OH or —NH$_2$ and $R_3$, $R_4$, $R_5$ and $R_6$ =H, and the addition salts of these compounds with pharmaceutically acceptable acids, in admixture with a pharmaceutically acceptable excipient.

2. The pharmaceutical composition as claimed in claim 1, comprising an effective amount of a compound chosen from the compounds of formula I and of formula II in which $R_1$, $R_3$ and $R_4$ are chosen from hydrogen, halogens, hydroxyl, —CHO, —OR, —COOH, —CN, —CO$_2$R, —CONHR, —CONRR', —NH$_2$, —N(R)$_2$, —NHR, —NH—CH$_2$—CH$_2$—N(CH$_3$)$_2$, —NHCOR, morpholino, nitro and —SO$_3$H groups, $R_2$ is chosen from nitro and —NHCOCF$_3$ groups, and the addition salts of these compounds with pharmaceutically acceptable acids.

3. The pharmaceutical composition as claimed in claim 2, comprising an effective amount of a compound chosen from the compounds of formula I in which $R_1$ is chosen from hydrogen and methoxy and —N(CH$_3$)$_2$ groups and the compounds of formula II in which $R_1$ is chosen from hydrogen and methoxy, —N(CH$_3$)$_2$ and —NHCOCH$_3$ groups and $R_2$ is an —NHCOCF$_3$ group, and the addition salts of these compounds with pharmaceutically acceptable acids.

4. The pharmaceutical composition as claimed in claim 2, comprising an effective amount of a compound chosen from the compounds of formula I in which $R_3$ is a —COOEt group and the compounds of formula II in which $R_3$ is a —COOEt group and $R_2$ is chosen from —NHCOCF$_3$ and —NO$_2$ groups, and the addition salts of these compounds with pharmaceutically acceptable acids.

5. The pharmaceutical composition as claimed in claim 2, comprising an effective amount of a compound chosen from the compounds of formula I in which $R_4$ is a methoxy group and the compounds of formula II in which $R_4$ is a methoxy group and $R_2$ is chosen from —NHCOCF$_3$ and —NO$_2$ groups, and the addition salts of these compounds with pharmaceutically acceptable acids.

6. A compound which is selected from the group consisting of:

4-(2-trifluoroacetamidophenyl)pyrido[3,2-g]quinoline-5,10-dione, 6-methoxy-4-(2-trifluoroacetamidophenyl)pyrido-[3,2-g]quinoline-5,10-dione, 6-(dimethylamino)-4-(2-trifluoroacetamidophenyl)-pyrido[3,2-g]quinoline-5,10-dione, 6-(acetamido)-4-(2-trifluoroacetamidophenyl)pyrido-[3,2-g]quinoline-5,10-dione, 8-methoxy-4-(2-trifluoroacetamidophenyl)pyrido-[3,2-g]quinoline-5,10-dione, ethyl 4-(2-trifluoroacetamidophenyl)-5,10-dioxo-pyrido[3,2-g]quinoline-7-carboxylate, 8-methoxy-4-(2-nitrophenyl)pyrido[3,2-g]quinoline-5,10-dione, ethyl 4-(2-nitrophenyl)-5,10-dioxopyrido[3,2-g]-quinoline-7-carboxylate, benzo[b]pyrido[4,3,2-de][1,7]phenanthroline-8-one, 12-dimethylaminobenzo[b]pyrido[4,3,2-de][1,7]-phenanthroline-8-one, 10-hydroxybenzo[b]pyrido[4,3,2-de][1,7]phenanthroline-8-one, 10-methoxybenzo[b]pyrido[4,3,2-de][1,7]phenanthroline-8-one, 11-ethylbenzo[b]pyrido[4,3-de][1,7]phenanthrolinecarboxylate-8-one, and the salts thereof with pharmaceutically acceptable acids.

7. A method for treating a patient with a solid tumor, comprising the administration to this patient of an effective amount of a compound chosen from the compounds of formulae:

Formula I

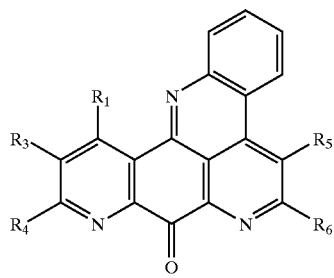

Formula II

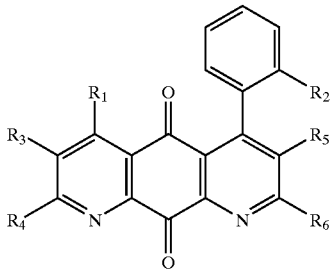

in which:

$R_1$, $R_3$, $R_4$, $R_5$ and $R_6$ are chosen from hydrogen, halogens and hydroxyl, —CHO, —OR, —COOH, —CN, —CO$_2$R, —CONHR, —CONRR',

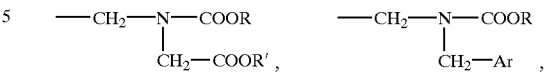

—NH$_2$, —NHR, —N(R)$_2$, —NH—CH$_2$—CH$_2$—N(CH$_3$)$_2$, —NHCOR, morpholino, nitro and —SO$_3$H groups, R and R' being chosen from C$_1$–C$_6$ alkyl groups and Ar being a C$_6$–C$_{14}$ aryl group, $R_2$ is chosen from nitro and —NHCOCF$_3$ groups, with the exclusion of the compounds of formula I in which $R_1$=—OH or —NH$_2$ and $R_3$, $R_4$, $R_5$ and $R_6$=H, and the addition salts of these compounds with pharmaceutically acceptable acids.

8. The pharmaceutical composition as claimed in claim 1, wherein $R_1$ is other than an —OR group.

9. The pharmaceutical composition as claimed in claim 1, wherein $R_1$ is —OR.

* * * * *

UNITED STATES PATENT AND TRADEMARK OFFICE
CERTIFICATE OF CORRECTION

PATENT NO.    : 6,583,150 B1
DATED         : June 24, 2003
INVENTOR(S)   : Delfourne et al.

It is certified that error appears in the above-identified patent and that said Letters Patent is hereby corrected as shown below:

<u>Title page,</u>
Item [73], Assignee, "Laboratorie L. Lafon" should be -- Laboratoire L. Lafon --.

Signed and Sealed this

Second Day of December, 2003

JAMES E. ROGAN
*Director of the United States Patent and Trademark Office*